United States Patent [19]

Kiel et al.

[11] Patent Number: 5,156,971

[45] Date of Patent: Oct. 20, 1992

[54] RAPID IDENTIFICATION OF ENVIRONMENTAL BACILLUS

[76] Inventors: Johnathan L. Kiel; John L. Alls; Richard A. Weber; Jill E. Parker, all of AL/OEDR Brooks AFB, San Antonio, Tex. 78235-5000

[21] Appl. No.: 821,525

[22] Filed: Jan. 15, 1992

[51] Int. Cl.$^5$ .............. C12N 1/22; C12N 5/00; A61K 43/00

[52] U.S. Cl. .............. 435/252.31; 435/240.31; 424/1.1; 424/9; 534/573; 534/769; 534/767; 534/789

[58] Field of Search .............. 435/832, 34, 240.31; 424/1.1, 9; 534/573, 769, 767, 789

[56] References Cited

U.S. PATENT DOCUMENTS 5,003,050  3/1991  Kiel .................. 435/7.2

OTHER PUBLICATIONS

Kim et al., J. Applied Bacteriology, 37, 265-267 1974.
Greene et al., J. Bacteriology, vol. 171, No. 1, pp. 104-113 1989.
Kniseley, J. Bacteriology, vol. 90, No. 6, pp. 1778-1783 1965.
Kniseley, J. Bacteriology, vol. 92, No. 3, pp. 784-786 1966.
Tittball et al., J. Applied Bacteriology, 62: 269-273.
Ristroph et al., Infection & Immunity 39:1:483-486.
Miller et al., Applied & Environmental Microbiology vol. 35, No. 4, 813-816.

*Primary Examiner*—Douglas W. Robinson
*Assistant Examiner*—Jane Williams
*Attorney, Agent, or Firm*—Charles E. Bricker; Donald J. Singer

[57] ABSTRACT

A diagnostic test for environmental bacillus which comprises the steps of inoculating an agar growth medium comprising a nitrate source, luminol and 3-amino-L-tyrosine (3AT) with the sample, incubating the inoculated medium and determining the presence of the bacillus. The novel medium preferably comprises potassium nitrate, luminol, 3-amino-L-tyrosine and trypticase soy agar. Antibiotics and/or a specific bacteriophage may be added to the medium surface in localized areas to show specific bacterial lysis for identification. The novel medium and the methods of this invention are suitable for the identification of B. anthracis.

1 Claim, No Drawings

RAPID IDENTIFICATION OF ENVIRONMENTAL BACILLUS

RIGHTS OF THE GOVERNMENT

The invention described herein may be manufactured and used by or for the Government of the United States for all governmental purposes without the payment of any royalty.

BACKGROUND OF THE INVENTION

This invention relates to a method for the identification and quantification of environmental bacillus.

Anthrax is an acute infectious disease, primarily of animals, although humans can be infected. Anthrax is caused by Bacillus anthracis, a spore-forming bacterium.

The most susceptible animals are the herbivores. The disease occurs when spores of B. anthracis are eaten in forage. Usually septicemia, or blood poisoning, occurs. The effects vary from a sudden attack, with death occurring a few minutes after the appearance of the first symptoms, to a subacute but eventually fatal illness manifesting fever, an enlarged spleen, and frequently intestinal disturbances. In humans, the disease occurs almost exclusively from contact with animals or animal products.

Bacillus anthracis is gram-positive, rod-shaped, 3–8 $\mu$m in length by 1–1.2 $\mu$m in diameter. In infected animals, the microorganism occurs as chains of 2–8 bacilli surrounded by a large capsule. When grown on artificial media, the chains contain more bacilli, and the capsule is lost. Under conditions unfavorable for growth, the bacilli form small, ellipsoidal spores which are very resistant to temperature extremes and to dehydration. The spores, which remain capable of growth for about 12 years, are ingested by animals grazing on pastureland contaminated with the droppings of sick animals.

In recent years, anthrax has been of minor importance to the livestock industry and even a lesser threat to the human population. Between 1974 and 1977 there were over 100 laboratory confirmed cases in Texas. Nationwide, during the same period, there were 6 cases of human anthrax, with 1 death.

Anthrax in cattle usually occurs during the warm, dry, summer months, when grass is short and dusty conditions prevail, although isolated cases have been reported throughout the year. The perpetuation of anthrax in a livestock population is commonly a sequential cycle involving spores—susceptible herbivorous host—disease—death—dissemination of organisms from the carcass—spores.

Laboratory procedures for the diagnosis of anthrax generally comprise incubation of blood smeared or tissue impressed agar plates with visual identification of the so-called "string of pearls". One such procedure (Whitford, H. W. "Factors Affecting the Laboratory Diagnosis of Anthrax", *J. American Veterinary Medical Association*, 173(11), pp. 1467–1469) comprises four agar plates. The first plate (Plate I) is a tryptose agar plate. This plate is streaked with suspect material (blood, tissue or bacterial colony), then a penicillin-impregnated disk is placed on the agar. A glass cover slip is placed over the streaked area, adjacent to the penicillin disk. The additional plates contain 5% bovine blood. One-half of one of these plates (Plate II) is streaked with the suspect material. On the other half of this plate, a known culture of B. anthracis (Sterne's vaccine strain) is streaked. To each half of the plate a 10-unit penicillin-impreganted disk and a drop of a suspension of specific bacteriophage are placed. The other two blood agar plates (Plates III and IV) are routinely streaked for isolation of bacterial colonies.

Plate I is incubated at 37° C. After 2½ to 3 hours, the area under the cover slip is examined microscopically (×1000) for the formation of chains of swollen, rounded B. anthracis cells. The number of cells in the chain varies from a few to many, depending on the time of incubation and the diffusion rate of penicillin in the agar.

With regard to Plate II, after incubation at 37° C. for 6 to 8 hours, most cultures have sparse growth of the organism on the plate but not in zones surrounding the penicillin disk or in the area of the bacteriophage. The Sterne vaccine strain acts as a positive control for both the penicillin disk and the bacteriophage lysis.

Plate III is incubated aerobically and Plate IV is incubated in a Brewer's anaerobic jar. Both are incubated overnight at 37° C. and are checked for other bacterial pathogens in the event B. anthracis is not detected in Plates I and II.

Problems can arise in diagnosis when the sample is contaminated. For example, contaminants such as non-pathogenic Bacillus spp and Clostridium spp closely resemble the vegetative form of B. anthracis. Thus, a laboratory technician, unskilled in diagnosis of anthrax, may misdiagnose the sample.

Accordingly, it is an object of this invention to provide a diagnostic test for environmental bacillus.

Other objects and advantages of the invention will be apparent to those skilled in the art.

SUMMARY OF THE INVENTION

In accordance with the present invention there is provided a diagnostic test for environmental bacillus which comprises the steps of inoculating an agar growth medium comprising a nitrate source, luminol and 3-amino-L-tyrosine (3AT) with said sample, incubating the inoculated medium and determining the presence of the bacillus. The novel medium preferably comprises potassium nitrate, luminol, 3-amino-L-tyrosine and trypticase soy agar. In one embodiment of the invention the potassium nitrate, luminol, 3-amino-L-tyrosine and trypticase soy agar are present in a weight ratio of 12:0.1:0.08:40 (600:5:4:2000 in whole numbers). Antibiotics such as penicillin, ampicillin, cloxacillin or methicillin, and/or a specific bacteriophage may be added to the medium surface in localized areas to show specific bacterial lysis for identification.

The bacillus can be isolated and identified from air and water samples collected on bacteriological filters, or directly from water, food, surfaces or biological samples. The novel medium of this invention supresses many environmental contaminating organisms.

The bacillus produces diazoluminomelanin (DALM) intracellularly and extracellularly in the medium without carbon dioxide or anaerobic incubation. DALM is discussed in Kiel et al, U.S. Pat. No. 5,003,050, issued Mar. 26, 1991. Biosynthesis of DALM in E. coli is discussed in Kiel et al, U.S. Pat. No. application Ser. No. 07/779,694, filed Oct. 21, 1991. The bacillus may then be made luminescent by the addition of a carbonate source, e.g., sodium carbonate or bicarbonate, and hydrogen peroxide, followed by heating to about 37° to 45° C. Luminometric measurements may be made using a luminometer, e.g., a TD-20e luminometer (Turner Designs, Mountain View, CA).

The novel medium of this invention allows for rapid development of the antibiotic test. Generally, if bacilli are present, the antibiotic test many be read within about one to two hours. The bacteriophage test can be read on this medium within about 4 hours.

Various modifications may be made to the invention as described without departing from the spirit of the invention or the scope of the appended claims.

We claim:

1. A novel medium for the growth and identification of environmental bacillus which comprises potassium nitrate, luminol, 3-amino-L-tyrosine and trypticase soy agar present in a weight ratio of about 600:5:4:2000, respectively.

* * * * *